United States Patent
Chen et al.

(10) Patent No.: US 12,138,620 B2
(45) Date of Patent: Nov. 12, 2024

(54) HIGHLY ACTIVE AND HIGHLY SELECTIVE COPPER EXTRUDATE CATALYSTS

(71) Applicant: BASF CORPORATION, Florham Park, NJ (US)

(72) Inventors: Jian-Ping Chen, Beachwood, OH (US); Scott Hedrick, Beachwood, OH (US); Jeffrey S. Baciak, Beachwood, OH (US); Bernd Bastian Schaack, Ludwigshafen (DE)

(73) Assignee: BASF Corporation, Florham Park, NJ (US)

( * ) Notice: Subject to any disclaimer, the term of this patent is extended or adjusted under 35 U.S.C. 154(b) by 673 days.

(21) Appl. No.: 17/297,603

(22) PCT Filed: Nov. 25, 2019

(86) PCT No.: PCT/US2019/063101
§ 371 (c)(1),
(2) Date: May 27, 2021

(87) PCT Pub. No.: WO2020/117532
PCT Pub. Date: Jun. 11, 2020

(65) Prior Publication Data
US 2022/0023843 A1 Jan. 27, 2022

Related U.S. Application Data

(60) Provisional application No. 62/774,609, filed on Dec. 3, 2018.

(51) Int. Cl.
*B01J 21/08* (2006.01)
*B01J 6/00* (2006.01)
*B01J 21/16* (2006.01)
*B01J 23/00* (2006.01)
(Continued)

(52) U.S. Cl.
CPC .............. *B01J 23/78* (2013.01); *B01J 6/001* (2013.01); *B01J 21/08* (2013.01); *B01J 35/613* (2024.01); *B01J 37/04* (2013.01); *C07C 29/154* (2013.01)

(58) Field of Classification Search
CPC . B01J 21/08; B01J 21/16; B01J 23/002; B01J 23/04; B01J 23/06; B01J 23/34;
(Continued)

(56) References Cited

U.S. PATENT DOCUMENTS

| | | | | |
|---|---|---|---|---|
| 3,560,406 A | * | 2/1971 | Juguin | C07C 45/002 568/376 |
| 4,598,058 A | * | 7/1986 | Frank | C07C 209/48 568/864 |

(Continued)

FOREIGN PATENT DOCUMENTS

CN 107635660 A 1/2018

OTHER PUBLICATIONS

International Search Report for PCT/U2019/063101 mailed Mar. 17, 2020, 4 pages.

*Primary Examiner* — Cam N. Nguyen
(74) *Attorney, Agent, or Firm* — Peter DiMauro

(57) ABSTRACT

A hydrogenation catalyst includes copper oxide, an alkali metal, and an acid-stabilized silica, wherein hydrogenation catalyst has a Brunauer-Emmett-Teller ("BET") surface area of greater than or equal to about 15 m2/g. The hydrogenation catalysts are effective for converting aldehydes, ketones, and esters to alcohols and/or diesters to diols.

20 Claims, 5 Drawing Sheets

(51) Int. Cl.
*B01J 23/04* (2006.01)
*B01J 23/06* (2006.01)
*B01J 23/34* (2006.01)
*B01J 23/72* (2006.01)
*B01J 23/74* (2006.01)
*B01J 23/75* (2006.01)
*B01J 23/755* (2006.01)
*B01J 23/76* (2006.01)
*B01J 23/78* (2006.01)
*B01J 23/80* (2006.01)
*B01J 23/889* (2006.01)
*B01J 35/10* (2006.01)
*B01J 35/61* (2024.01)
*B01J 37/04* (2006.01)
*C07C 29/154* (2006.01)

(58) Field of Classification Search
CPC . B01J 23/72; B01J 23/74; B01J 23/415; B01J 23/75; B01J 23/755; B01J 23/76; B01J 23/78; B01J 23/80; B01J 23/8892; B01J 35/1014; B01J 35/613; B01J 37/04; C07C 29/154
See application file for complete search history.

(56) References Cited

U.S. PATENT DOCUMENTS

| | | | |
|---|---|---|---|
| 5,124,295 A | 6/1992 | Nebesh et al. | |
| 5,756,808 A * | 5/1998 | Flick | B01J 23/8898 |
| | | | 558/459 |
| 5,801,268 A * | 9/1998 | Flick | B01J 23/78 |
| | | | 558/459 |
| 6,049,008 A | 4/2000 | Roberts et al. | |
| 6,114,567 A * | 9/2000 | Flick | B01J 23/8898 |
| | | | 558/459 |
| 9,006,129 B2 * | 4/2015 | Madon | B01J 23/8437 |
| | | | 502/244 |
| 9,169,192 B2 * | 10/2015 | Harada | B01J 37/18 |
| 9,308,522 B2 * | 4/2016 | Madon | B01J 37/06 |
| 9,381,467 B2 * | 7/2016 | Murawaki | F01N 3/281 |
| 2015/0105479 A1 * | 4/2015 | Schafer | B01J 29/06 |
| | | | 502/64 |
| 2016/0038917 A1 | 2/2016 | Thakur et al. | |
| 2022/0152596 A1 * | 5/2022 | Chen | B01J 35/0066 |
| 2023/0249160 A1 * | 8/2023 | Chen | B01J 23/005 |
| | | | 568/885 |

* cited by examiner

HIGHLY ACTIVE AND HIGHLY SELECTIVE COPPER EXTRUDATE CATALYSTS

CROSS-REFERENCE TO RELATED APPLICATIONS

This application is a national stage entry of International Application No. PCT/US2019/063101, filed Nov. 25, 2019, which claims the benefit of, and priority to, U.S. Provisional Application No. 62/774,609, filed Dec. 3, 2018, the contents of which are incorporated by reference herein in their entirety.

FIELD

The present technology relates to catalysts that are useful as hydrogenation catalysts, and more particularly, catalysts that are useful for hydrogenating ketone compounds to form alcohols. The invention also relates to a method of preparing such catalysts and to the use of such catalysts in hydrogenation reactions.

BACKGROUND

Hydrogenation is a chemical reaction that involves the addition of hydrogen ($H_2$) and is used in large scale industrial processes or smaller scale laboratory procedures. Copper is a known catalyst for hydrogenation reactions. U.S. Pat. No. 6,049,008 (Roberts), for example, is directed to chromium-free copper catalysts. U.S. Pat. No. 5,124,295 (Nebesh), for example, is directed to copper chromite catalysts. An exemplary carbonyl is a ketone, such as acetophenone, which can be hydrogenated to form an industrially useful feedstock, phenyl ethanol, according to hydrogenation reaction (1).

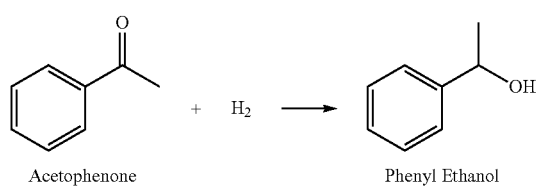

(1)

Acetophenone      Phenyl Ethanol

Many current commercial processes operate at high pressures, for example, in the range of 75-80 bar, to convert acetophenone to phenyl ethanol. For lower operating costs and increased safety measures, there is a desire to operate such processes at lower pressures in fixed bed reactors. In addition, there is a need to provide catalysts that show at least the same, if not better, activity and selectivity over conventional copper chromium catalysts. Undesired reactions, one of which is shown in reaction (2) for example result in by-products that cause fouling of the catalyst and reactor. Reaction (2) shows dehydration of the alcohol to an olefin followed by hydrogenation to a hydrocarbon.

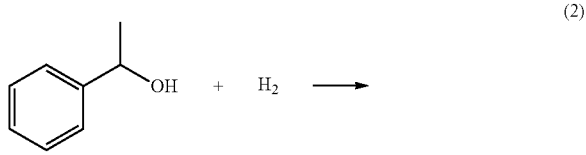

(2)

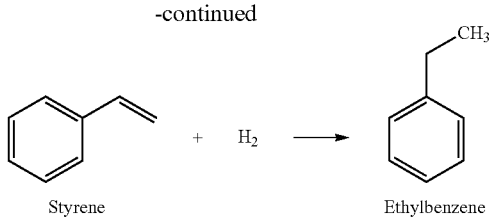

Styrene      Ethylbenzene

There is a continuing need to provide catalysts that maximize desired hydrogenation products while eliminating by-product formation and are free of chromium. It is also desirable to provide hydrogenation catalysts, methods for their manufacture and methods of use, which exhibit higher catalytic activity than existing catalysts.

SUMMARY

In one aspect, a hydrogenation catalyst is provided that includes copper oxide, an alkali metal, and an acid-stabilized silica, wherein hydrogenation catalyst has a Brunauer-Emmett-Teller ("BET") surface area of greater than or equal to about 15 $m^2/g$.

In one aspect, methods of making the catalyst for is provided, the method includes mixing a copper oxide and a clay material to obtain a dry material mixture; combining the dry material mixture with an aqueous acid-stabilized silica solution, a caustic material, and water to obtain a wet material mixture; and calcining the wet material mixture at a temperature, and for a time, sufficient to cure form a calcined hydrogenation catalyst; wherein: the calcined hydrogenation catalyst has a Brunauer-Emmett-Teller ("BET") surface area of greater than or equal to about 45 $m^2/g$; and the acid-stabilized silica solution has a pH of less than about 3.5.

In another aspect, the present technology provides a catalyst for hydrogenation as prepared by the method described herein in any embodiment.

In an aspect, methods of hydrogenating a ketone or aldehyde are provided, where the methods include method of hydrogenating a ketone, the method comprising contacting the ketone with a hydrogenation catalyst as described herein in any embodiment.

In another aspect, methods of synthesizing butanediol are provided, the methods include contacting a stream of dimethyl maleate with a hydrogenation catalyst as described herein in any embodiment.

In another aspect, methods of hydrogenating an ester are provided, the methods include method of hydrogenating an ester, the method comprising contacting the ester with a hydrogenation catalyst as described herein in any embodiment.

DETAILED DESCRIPTION

Figure 1:
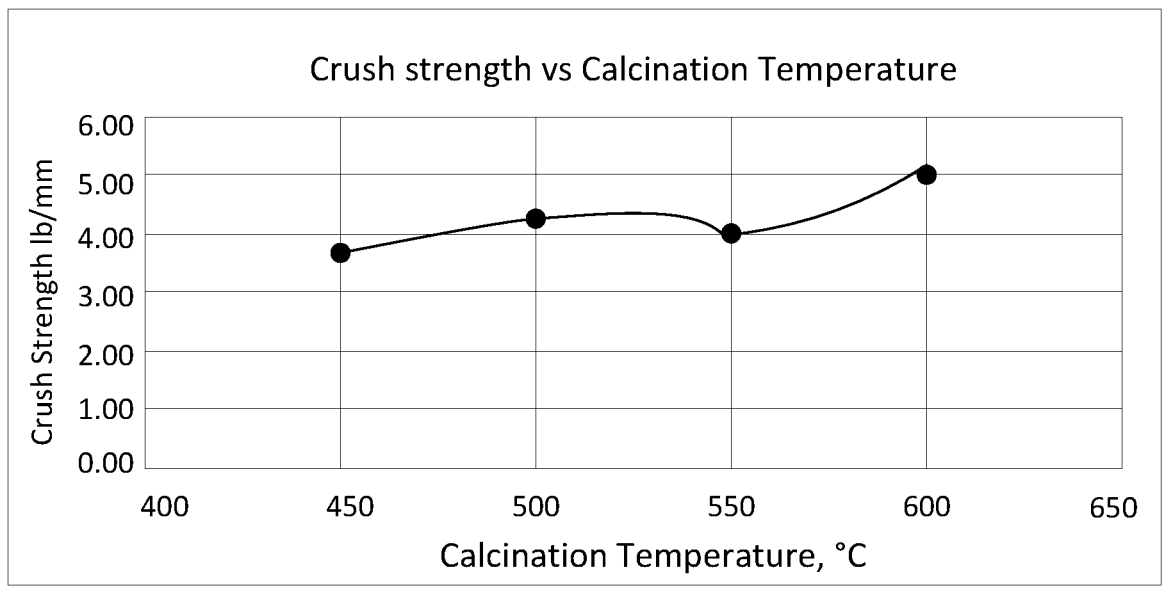
FIG. 1 illustrates a graph showing the effect of calcination temperature (° C.) on crush strength (lb/mm) for Example Catalysts 1A-1D.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

In general, "substituted" refers to an alkyl, alkenyl, cycloalkyl, or aryl group, as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group will be substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, alkynoxy, aryloxy, aralkyloxy, heterocyclyloxy, and heterocyclylalkoxy groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

As used herein, "alkyl" groups include straight chain and branched alkyl groups having from 1 to about 20 carbon atoms, and typically from 1 to 12 carbons or, in some embodiments, from 1 to 8 carbon atoms. As employed herein, "alkyl groups" include cycloalkyl groups as defined below. Alkyl groups may be substituted or unsubstituted. Examples of straight chain alkyl groups include methyl, ethyl, n-propyl, n-butyl, n-pentyl, n-hexyl, n-heptyl, and n-octyl groups. Examples of branched alkyl groups include, but are not limited to, isopropyl, sec-butyl, t-butyl, neopentyl, and isopentyl groups. Representative substituted alkyl groups may be substituted one or more times with, for example, amino, thio, hydroxy, cyano, alkoxy, and/or halo groups such as F, Cl, Br, and I groups. As used herein the term haloalkyl is an alkyl group having one or more halo groups. In some embodiments, haloalkyl refers to a per-haloalkyl group.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 6, or 7. Cycloalkyl groups may be substituted or unsubstituted. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups may be mono-substituted or substituted more than once, such as, but not limited to: 2,2-; 2,3-; 2,4-; 2,5-; or 2,6-disubstituted cyclohexyl groups or mono-, di-, or tri-substituted norbornyl or cycloheptyl groups, which may be substituted with, for example, alkyl, alkoxy, amino, thio, hydroxy, cyano, and/or halo groups.

Alkenyl groups are straight chain, branched or cyclic alkyl groups having 2 to about 20 carbon atoms, and further including at least one double bond. In some embodiments alkenyl groups have from 2 to 12 carbons, or, typically, from 2 to 8 carbon atoms. Alkenyl groups may be substituted or unsubstituted. Alkenyl groups include, for instance, vinyl, propenyl, 2-butenyl, 3-butenyl, isobutenyl, cyclohexenyl, cyclopentenyl, cyclohexadienyl, butadienyl, pentadienyl, and hexadienyl groups among others. Alkenyl groups may be substituted similarly to alkyl groups. Divalent alkenyl groups, i.e., alkenyl groups with two points of attachment, include, but are not limited to, CH—CH=CH$_2$, C=CH$_2$, or C=CHCH$_3$.

As used herein, "aryl", or "aromatic," groups are cyclic aromatic hydrocarbons that do not contain heteroatoms. Aryl groups include monocyclic, bicyclic and polycyclic ring systems. Thus, aryl groups include, but are not limited to, phenyl, azulenyl, heptalenyl, biphenylenyl, indacenyl, fluorenyl, phenanthrenyl, triphenylenyl, pyrenyl, naphthacenyl, chrysenyl, biphenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. The phrase "aryl groups" includes groups containing fused rings, such as fused aromatic-aliphatic ring systems (e.g., indanyl, tetrahydronaphthyl, and the like). Aryl groups may be substituted or unsubstituted.

Reference to a transition metal component means a material used to deliver a metal, for example metal oxides, which may be in solid or granular form. Thus, copper, manganese, zinc, nickel, cobalt, and/or iron may be delivered by their respective oxides.

Reference to an "alkali metal component" or an "alkaline earth metal component" means a material used to deliver an alkali metal or an alkaline earth metal, for example metal hydroxides or carbonates, which may be in powder form or in an aqueous solution.

Reference to "inorganic matrix component" means a material suitable for binding components together to form a catalyst in a shape. Generally, the inorganic matrix component is extrudable and used to form extruded catalysts and/or the inorganic matrix component is able to form tableted catalysts. Thus, the inorganic matrix component, or binder material, may include silica, zinc oxide, zirconium oxide, clay such as Bentonite, silicates such as calcium silicate, etc., and mixtures thereof. In a preferred embodiment, the silica source is silica sol. Suitable clays include Attapulgite.

All references to pore diameters and pore volumes in the specification and claims of this application are based upon measurements utilizing mercury porosimetry. A typical method is described by R. Anderson, Experimental Methods in Catalytic Research, Academic Press, New York, 1968. The pore volumes are determined utilizing the catalysts in their oxide forms. That is, the pore diameters and pore volumes reported herein are obtained for the catalyst after calcination, but prior to any reduction of the oxide. Those skilled in the art often refer to the catalyst containing the metal oxides as the "oxide" or "oxide precursor" form of the catalyst.

The catalysts of the present technology are based upon a high Brunauer-Emmett-Teller ("BET") surface area copper oxide and an acid-stabilized silica solution. Formation of the catalysts includes mixing and extruding of the precursor materials, followed by drying and calcination. Other additives may be included in the mixtures to form the catalysts.

The catalysts described herein exhibit higher catalytic hydrogenation and hydrogenolysis activity, and are more environmentally benign than the current commercially available catalysts based on copper-chromium (CuCr). The catalysts may be readily adopted and used in replacement of the CuCr catalysts, especially for hydrogenation of carbonyl compounds in styrene monomer and propylene ("SMPO") processes where chromium-containing catalysts are used.

The new catalysts also exhibit significant activity and selectivity for the hydrogenation of esters to corresponding alcohols, such as, dimethyl maleate ("DMM") to butanediol ("BDO"). The reaction sequence is shown below in Scheme 1.

Scheme 1

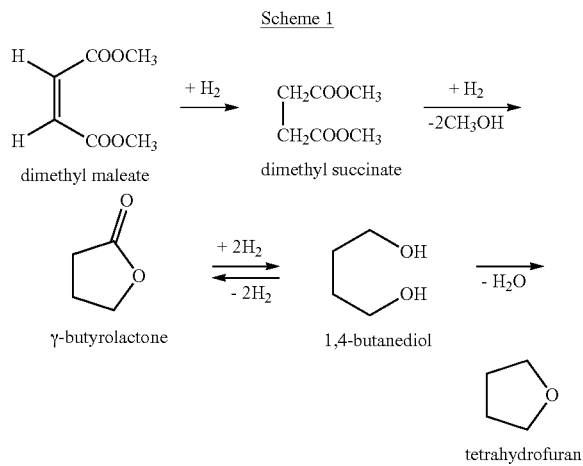

The first step is hydrogenation of DMM to dimethyl succinate (DMS) which in turn undergoes hydrogenolysis to form γ-butyrolactone (gBL) which can be further hydrogenated to 1,4-butanediol (BDO), the desired product in this case. Subsequent dehydration of BDO will form tetrahydrofuran (THF) and possibly trace amounts of n-butanol (not shown). The catalysts for hydrogenation described herein exhibit low packed bulk density and strong mechanical strength which provide the added benefits of lower costs and longer catalyst life, when compared to the current, state of the art materials that are used.

Provided are hydrogenation catalysts that are useful for hydrogenating carbonyl compounds to form alcohols, respectively. Exemplary carbonyl compounds are ketones and aldehydes. Methods of making and using the same are also provided. These catalysts are formed from a catalytic material and an inorganic matrix component, which are processed together, for example, by extrusion or by tableting, to form the catalyst. The catalytic material comprises a copper oxide in combination with an alkali metal component and optionally an alkaline earth metal component. The inorganic matrix component is formed from at least a silica component (e.g., silica sol). Without intending to be bound by theory, the use of an alkali metal component results in a catalyst having excellent selectivity and activity for hydrogenation. Further delivering the alkali metal component separately from the silica component, for example sodium hydroxide and silica sol, respectively, rather than using an alkali silicate such as sodium silicate, results in a catalyst having a content of mesopores that facilitates the hydrogenation reactions and extends catalyst life.

Catalysts disclosed herein in extruded form show improved crush strength as compared to extruded catalysts formed using sodium silicate as a single source of both the alkali metal and the silica.

Catalyst Composition

In one aspect, a hydrogenation catalyst that includes copper oxide, an alkali metal, and an acid-stabilized silica, wherein hydrogenation catalyst has a Brunauer-Emmett-Teller ("BET") surface area of greater than or equal to about 15 m$^2$/g.

In any embodiment herein, the hydrogenation catalyst has a BET surface area of greater than about 15 m$^2$/g. In any embodiment herein, the hydrogenation catalyst has a BET surface area greater than about 20 m$^2$/g. In any embodiment herein, the hydrogenation catalyst has a BET surface area of greater than about 30 m$^2$/g. In any embodiment herein, the hydrogenation catalyst has a BET surface area of greater than about 45 m$^2$/g. In any embodiment herein, the hydrogenation catalyst may have a BET surface area of about 15 m$^2$/g to about 70 m$^2$/g. In any embodiment herein, the hydrogenation catalyst may have a BET surface area of about 30 m$^2$/g to about 70 m$^2$/g. In any embodiment herein, the hydrogenation catalyst has a BET surface area of about 45 m$^2$/g to about 70 m$^2$/g. For example, in any embodiment herein, the hydrogenation catalyst has a BET surface area of about 15 m$^2$/g, about 20 m$^2$/g, about 25 m$^2$/g, about 30 m$^2$/g, about 35 m$^2$/g, about 40 m$^2$/g, about 45 m$^2$/g, about 50 m$^2$/g, about 55 m$^2$/g, about 60 m$^2$/g, about 65 m$^2$/g, about 70 m$^2$/g, or any range including and/or in between any two of the preceding values. In any embodiment herein, the hydrogenation catalyst has a BET surface area of about 15 m$^2$/g to about 70 m$^2$/g, about 30 m$^2$/g to about 70 m$^2$/g, about 45 m$^2$/g to about 65 m$^2$/g, about 45 m$^2$/g to about 60 m$^2$/g, about 50 m$^2$/g to about 60 m$^2$/g, or any range including and/or in between any two of the preceding values.

In any embodiment herein, the hydrogenation catalyst includes the copper oxide in an amount from about 50.0 wt % to about 90.0 wt % by weight of the hydrogenation catalyst. Suitable amounts of the copper oxide may include, but are not limited to, about 50.0 wt % to about 90.0 wt %, about 65.0 wt % to about 85.0 wt %, about 70.0 wt % to about 80.0 wt %, or any range including and/or in between any two of the preceding values. For example, in any embodiment herein, the amount of the copper oxide may include, but is not limited to, about 50.0 wt %, about 55.0 wt %, about 60.0 wt %, about 65.0 wt %, about 70.0 wt %, about 75.0 wt %, about 80 wt %, or any range including and/or in between any two of the preceding values.

In any embodiment herein, the alkali metal is selected from the group consisting of sodium (Na), potassium (K), rubidium (Rb), cesium (Cs), and combinations thereof. These metals may be present in the reduced metal or oxide forms or as precursors to such forms and in one or more oxidation states as discussed above. For example, in any embodiment herein, the alkali metal component may include sodium in the form of disodium oxide. In any embodiment herein, the alkali metal component is present in an amount from 0 wt % to about 8.0 wt % by weight of the hydrogenation catalyst. For example, in any embodiment herein, the alkali metal component may be present in an amount from about 0.01 wt %, about 0.1 wt %, about 1.0 wt %, about 1.5 wt %, about 2.0 wt %, about 2.5 wt %, about 3.0 wt %, about 3.5 wt %, about 4.0 wt %, about 4.5 wt %, about 5.0 wt %, about 5.5 wt %, about 6.0 wt %, about 6.5 wt %, about 7.0 wt %, about 7.5 wt %, about 8.0 wt %, or any range including and/or in between any two of the preceding values. In any embodiment herein, the alkali metal component may be present in an amount from 0 wt % to about 8.0 wt %, about 1 wt % to about 6.5 wt %, about 3.0 wt % to about 5.0 wt %, or any range including and/or in between any two of the preceding values.

Without intending to be bound by theory, the use of an alkali metal component results in a catalyst having excellent selectivity and activity for hydrogenation. Further delivering the alkali metal component separately from the acid-stabilized silica, for example sodium hydroxide and silica sol, respectively, rather than using an alkali silicate such as sodium silicate, results in a catalyst having a content of mesopores that facilitates the hydrogenation reactions and extends catalyst life.

In any embodiment herein, the catalytic material may further include an alkaline earth metal component, where the alkaline earth metal is selected from the group consisting of magnesium (Mg), calcium (Ca), strontium (Sr), barium (Ba), and combinations thereof. These metals may be present in the reduced metal or oxide forms or as precursors to such forms and in one or more oxidation states as discussed above. For example, in any embodiment herein, the alkaline earth metal component may be calcium. In any embodiment herein, the alkaline earth metal component may include calcium oxide. The alkaline earth metal component may be present in an amount from about 1.0 wt % to about 18.0 wt %. For example, in any embodiment herein, the amount of calcium oxide may be about 1.0 wt %, about 1.5 wt %, about 2.0 wt %, about 2.5 wt %, about 3.0 wt %, about 3.5 wt %, about 4.0 wt %, about 4.5 wt %, about 5.0 wt %, about 5.5 wt %, about 6.0 wt %, about 6.5 wt %, about 7.0 wt %, about 7.5 wt %, about 8.0 wt %, about 8.5 wt %, about 9.0 wt %, about 9.5 wt %, about 10.0 wt %, about 10.5 wt %, about 11.0 wt %, about 12.0 wt %, about 13.0 wt %, about 14.0 wt %, about 15.0 wt %, about 16.0 wt %, about 17.0 wt %, about 18.0 wt %, or any range including and/or in between any two of the preceding values.

In any embodiment herein, the catalyst may further include an additional metal component. Reference to the transition metal component means a material used to deliver a metal, for example metal oxides, which may be in solid or granular form. Thus, manganese, zinc, nickel, cobalt, and/or iron may be delivered by their respective oxides. For example, in any embodiment herein, the transition metal component may include manganese, zinc, nickel, cobalt, iron, or a mixture of two or more thereof. In any embodiment herein, the transition metal component may be manganese. For example, in any embodiment herein, the transition metal component may be manganese oxide.

The transition metal component may be present in an amount from 0 wt % to about 5.0 wt %, from about 0.5 wt % to about 3.0 wt %, about 1.0 wt % to about 2.5 wt %, or any range including and/or in between any two of the preceding values. For example, in any embodiment herein, the transition metal component may be present in an amount of about 0.01 wt %, about 0.1 wt %, about 1.0 wt %, about 1.5 wt %, about 2.0 wt %, about 2.5 wt %, about 3.0 wt %, about 3.5 wt %, about 4.0 wt %, about 4.5 wt %, about 5.0 wt %, or any range including and/or in between any two of the preceding values.

The hydrogenation catalyst includes an acid-stabilized silica. In any embodiment herein, the acid-stabilized silica may have a pH of less than about 3.5. For example, in any embodiment therein, the acid-stabilized solution has a pH of less than about 3.5, less than about 3.3, less than about 2.9, less than about 2.7, less than about 2.5, or less than about 2.3. In any embodiment herein, the acid-stabilized silica may be formed from an acid-stabilized silica solution.

In any embodiment herein, the acid-stabilized silica may be present in an amount from about 5.0 wt % to about 20.0 wt %, from about 10.0 wt % to about 20.0 wt %, from about 12.0 wt % to about 15 wt %, or any range including and/or in between any two of the preceding values. For example, in any embodiment, the silica component may be present in an amount of about 5.0 wt %, about 6.0 wt %, about 7.0 wt %, about 8.0 wt %, about 9.0 wt %, about 10.0 wt %, about 11.0 wt %, about 12.0 wt %, about 13.0 wt %, about 14.0 wt %, about 15.0 wt %, about 16.0 wt %, about 17.0 wt %, about 18.0 wt %, about 19.0 wt %, about 20.0 wt %, or any range including and/or in between any two of the preceding values.

In any embodiment herein, the catalyst may further include crystalline silica. For example, in any embodiment herein, the catalyst may include crystalline silica in an amount from about 0 wt % to about 1.0 wt %. Suitable amounts include, but are not limited to, about 0.01 wt %, about 0.1 wt %, about 0.2 wt %, about 0.3 wt %, about 0.4 wt %, about 0.5 wt %, about 0.6 wt % about 0.7 wt %, about 0.8 wt %, about 0.9 wt %, about 1.0 wt %, or any range including and/or in between any two of the preceding values.

In any embodiment herein, the catalyst may further include from about 0 wt % to about 10 wt % of a clay material. In any embodiment herein, the clay material may include, but is not limited to, alumino-silicate clays such as attapulgites, sepiolites, serpentines, kaolinites, illite, playgorskite, montmorillonites, or mixtures thereof. For example, in any embodiment herein, the clay may be an alumino-silicate attapulgite clay. For purposes herein, the term "attapulgite" is used to mean chain lattice type clay minerals, encompassing minerals and mineral groups variously referred to in the literature as "attapulgite," "palygorskite," "sepiolite," and "hormite." Typically, the clays suitable for use in the instant invention contain a major amount of attapulgite. As used herein, "major amount" shall mean and refer to a component which is present in the largest amount of any of the components present.

Specifically, these catalysts contain a significant amount of mesoporosity. Reference to "mesoporosity" or "mesopore" means those pores having a pore diameter in the range of about 150 to about 2500 Angstroms (Å). For example, in any embodiment herein, the catalysts may have a pore diameter from about 150 Å to about 2500 Å, about 200 Å to about 2000 Å, about 225 Å to about 1500 Å, about 250 Å to about 1000 Å, about 300 Å to about 800 Å, or any range including and/or in between any two of the preceding values.

In any embodiment herein, the catalyst may have a pore volume that is greater than or equal to 0.25 cm$^3$/g. For example, in any embodiment herein, the catalyst may have a pore volume of about 0.25 cm$^3$/g, about 0.3 cm$^3$/g, about 0.35 cm$^3$/g, about 0.4 cm$^3$/g, about 0.45 cm$^3$/g, about 0.5 cm$^3$/g, about 0.55 cm$^3$/g, about 0.6 cm$^3$/g, about 0.65 cm$^3$/g, about 0.7 cm$^3$/g, about 0.75 cm$^3$/g, about 0.8 cm$^3$/g, or any range including and/or in between any two of the preceding values. In any embodiment herein, the catalyst may have a pore volume of about 0.25 cm$^3$/g to about 0.65 cm$^3$/g, about 0.3 cm$^3$/g to about 0.55 cm$^3$/g, about 0.35 cm$^3$/g to about 0.45 cm$^3$/g, or any range including and/or in between any two of the preceding values.

In any embodiment herein, the catalyst may have a packed bulk density of about 0.8 g/cm$^3$ to about 1.5 g/cm$^3$. For example, in any embodiment herein, the catalyst may have a packed bulk density of about 0.8 g/cm$^3$, about 0.9 g/cm$^3$, about 1 g/cm$^3$, about 1.1 g/cm$^3$, about 1.2 g/cm$^3$, about 1.3 g/cm$^3$, about 1.4 g/cm$^3$, about 1.5 g/cm$^3$, or any range including and/or in between any two of the preceding values. In any embodiment herein, the catalyst may have a packed bulk density of about 0.8 g/cm$^3$ to about 1.5 g/cm$^3$, about 0.8 g/cm to about 1 g/cm$^3$, about 0.8 g/cm$^3$ to about 0.95 g/cm$^3$, or any range including and/or in between any two of the preceding values.

In any embodiment herein, the catalyst is free of, or substantially free of, chromium or an oxide thereof. In addition, compositions are usually free of chromium in order to reduce exposure to such material. As used herein the catalyst is free of such materials if their presence is in an amount that does not materially affect the physical, chemical and catalytic characteristics of the compositions when compared to those which are completely free of such materials. Preferably, if present, such materials will be present in trace amounts, but in amounts not greater than about 1.5% by weight, more preferably not greater than 0.5% by weight. For example, in any embodiment herein, the phrase "substantially free of chromium" refers to less than about 1.5 wt %, less than about 1 wt %, less than about 0.5 wt %, less than about 0.1 wt %, less than about 0.01 wt %, or 0 wt % based on the total weight of the catalyst.

Catalysts can be provided as tablets or extrudates. One way to process the blend of all of the ingredients is to extrude it through a shaping orifice to form an extruded catalyst body, or extrudate. Other catalyst bodies can be shaped into spheres or any other convenient formation. Another way is to tablet the catalysts. For example, in any embodiment herein, the catalyst may be extruded or tabletted in sizes including, but not limited to, 1/8" by 1/8", 3/16" by 3/16", 1/4" by 1/4", 1/16" by 1/16", 3/16" by 1/4", 1/4" by 1/16", 1/8" by 1/16", 1/16", 1/16" 3F (3-fluted), 1/8", 1/8" 3F, 3/16", or 3/16" 3-F.

In any embodiment herein, the catalyst provided in tabletted or extruded form, may exhibit a crush strength in an amount from about 1.5 lbs/mm to about 6.0 lbs/mm. For example, in any embodiment herein, the catalyst may exhibit a side crush strength of about 1.5 lbs/mm, about 2.0 lbs/mm, about 2.5 lbs/mm, about 3.0 lbs/mm, about 3.5 lbs/mm, about 4.0 lbs/mm, about 4.5 lbs/mm, about 5.0 lbs/mm, about 5.5 lbs/mm, about 6.0 lbs/mm, or any range including and/or in between any two of the preceding values. In some embodiments, the catalyst may exhibit a side crush strength from about 3.5 lbs/mm to about 5.0 lbs/mm.

In any embodiment herein, the catalyst may be calcined. In any embodiment herein, the catalyst is a calcined and extruded catalyst.

In any embodiment herein, the catalyst may be in an unactivated form and exhibits an X-ray powder diffraction profile with 2θ peaks at 29.6°, 35.5°, 38.7°, and 58.9°. In any embodiment herein, the catalyst may be in an unactivated form and exhibits an X-ray powder diffraction profile with 2θ peaks at 26.7°, 29.6°, 35.5°, 38.7°, 58.9°, 53.4°, 68.2°, 61.6°, 66.3°, 68.0°, 72.3°, 75.1°, and 82.9°.

In any embodiment herein, the catalyst has a copper oxide crystallite size of about 60 Å to about 200 Å. For example, in any embodiment herein, the catalyst may have a copper oxide crystallite size of about 60 Å, about 65 Å, about 70 Å, about 75 Å, about 80 Å, about 85 Å, about 90 Å, about 95 Å, about 100 Å, about 105 Å, about 110 Å, about 120 Å, about 125 Å, about 130 Å, about 135 Å, about 140 Å, about 145 Å, about 150 Å, about 155 Å, about 160 Å, about 165 Å, about 170 Å, about 175 Å, about 180 Å, about 185 Å, about 190 Å, about 195 Å, about 200 Å, or any range including and/or in between any two of the preceding values. In any embodiment, the catalyst may have a copper oxide crystallite size of about 70 Å to about 165 Å.

Method of Making

In one aspect, methods of making the catalyst for hydrogenation described herein is provided. The method includes mixing a copper oxide and a clay material to obtain a dry material mixture; combining the dry material mixture with an aqueous acid-stabilized silica solution, a caustic material, and water to obtain a wet material mixture; and calcining the wet material mixture at a temperature, and for a time, sufficient to cure form a calcined hydrogenation catalyst; wherein: the calcined hydrogenation catalyst has a Brunauer-Emmett-Teller ("BET") surface area of greater than or equal to about 15 m$^2$/g; and the acid-stabilized silica solution has a pH of less than about 3.5.

The dry material mixture also includes a clay material. In any embodiment herein, the clay material may include, but is not limited to, alumino-silicate clays such as attapulgites, sepiolites, serpentines, kaolinites, playgorskite, calcium montmorillonites and mixtures thereof. For example, in any embodiment herein, the clay may be an alumino-silicate attapulgite clay.

The method may further include mixing a transition metal component into the dry material mixture. For example, in any embodiment herein, the transition metal component may include, but is not limited to, manganese, zinc, nickel, cobalt, iron, or a mixture of two or more thereof. The transition metal component may be in the form of a transition metal carbonate. In any embodiment herein, the transition metal component may be manganese. For example, in any embodiment herein, the manganese may be manganese carbonate.

In any embodiment herein, the method may further include mixing an alkaline earth metal component. The alkaline earth metal component may be an alkaline earth metal hydroxide or carbonate where the alkaline earth metal is selected from the group consisting of magnesium (Mg), calcium (Ca), strontium (Sr), barium (Ba), and combinations thereof. For example, in any embodiment herein, the alkaline earth metal component may be a calcium component. In any embodiment herein, the calcium component may be calcium hydroxide.

In any embodiment herein, the method may further include mixing one or more binders, extrusion aids, or a combination thereof in to the dry material mixture. Suitable binders or extrusion aids may include, but are not limited to, a polymeric polysaccharide, hydroxypropyl methyl cellulose, hydroxylethyl methyl cellulose, or a mixture of two or more thereof. For example, in any embodiment herein, the binder or extrusion aid may be selected from a commercially available binder or extrusion aid, including but not limited to, Zusoplast, Methocel, Walocel, or a mixture thereof.

The method includes combining the dry material mixture with an aqueous acid-stabilized silica solution component, a caustic material, and water. In any embodiment herein, the aqueous acid-stabilized silica solution may have a pH of less than about 3.5. For example, in any embodiment therein, the aqueous acid-stabilized solution has a pH of less than about 3.5, less than about 3.3, less than about 2.9, less than about 2.7, less than about 2.5, or less than about 2.3. A preferred silica sol that is an acid-stabilized silica solution is sold under the trade name Levasil CA320 DH having a pH from about 2.3 to about 3.3, a specific surface area of 200 m$^2$/g, a density of about 1.2 g/mL, a viscosity of about 7 cP, and 34% silica (as $SiO_2$).

In any embodiment herein, the caustic material may include, but is not limited to, an alkali metal. The alkali metal is an alkali metal hydroxide or carbonate where the alkali metal is selected from the group consisting of sodium (Na), potassium (K), rubidium (Rb), cesium (Cs), and combinations thereof. For example, in any embodiment herein, the alkali metal may be an alkali metal hydroxide, such as sodium hydroxide.

Upon combining the dry material mixture with the aqueous acid-stabilized silica, caustic material, and water, the resultant wet material mixture undergoes an exotherm reaction. Without wishing to be bound by theory, in an exemplary embodiment, an exothermic reaction between $Ca(OH)_2$, NaOH, and $SiO_2$ may occur during the drying step to cure the wet material matrix. This exothermic reaction is represented by the following chemical equation:

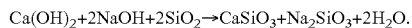

$$Ca(OH)_2 + 2NaOH + 2SiO_2 \rightarrow CaSiO_3 + Na_2SiO_3 + 2H_2O.$$

The method includes calcining the wet material mixture at a temperature, and for a time, sufficient to cure form a calcined hydrogenation catalyst. In any embodiment herein, the calcining may occur at a temperature from about 300° C. to about 750° C. For example, in any embodiment herein, the calcining may occur at a temperature of about 300° C., about 350° C., about 400° C., about 450° C., about 500° C., about 550° C., about 600° C., about 650° C., about 700° C., about 750° C., or any range including and/or in between any two of the preceding values. In any embodiment herein, the calcining temperature may be from about 400° C. to about 650° C., from about 400° C. to about 550° C., or from about 450° C. to about 500° C. In any embodiment herein, the calcination may occur over a period from about 0.5 h to about 4 h. In any embodiment, the calcination may occur over a period of about 0.5 h, about 1 h, about 1.5 h, about 2 h, about 2.5 h, about 3 h, about 3.5 h, about 4 h, or any range including and/or in between any two of the preceding values.

In any embodiment herein, the method may further include extruding or tableting the wet material mixture prior to calcining. For example, in any embodiment herein, the wet material mixture may be extruded or tableted in sizes including, but not limited to, ⅛" by ⅛", 3/16" by 3/16", ¼" by ¼", 1/16" by 1/16", 3/16" by ¼", ¼" by 1/16", ⅛" by 1/16", 1/16", 1/16" 3F (3-fluted), ⅛", ⅛" 3F, 3/16", or 3/16" 3-F.

In any embodiment herein, the catalyst provided in tableted or extruded form, may exhibit a crush strength in an amount from about 1.5 lbs/mm to about 6.0 lbs/mm. For example, in any embodiment herein, the catalyst may exhibit a side crush strength of about 1.5 lbs/mm, about 2.0 lbs/mm, about 2.5 lbs/mm, about 3.0 lbs/mm, about 3.5 lbs/mm, about 4.0 lbs/mm, about 4.5 lbs/mm, about 5.0 lbs/mm, about 5.5 lbs/mm, about 6.0 lbs/mm, or any range including and/or in between any two of the preceding values. In some embodiments, the catalyst may exhibit a side crush strength from about 3.5 lbs/mm to about 5.0 lbs/mm.

The method may further include removing at least some of the water from the wet material mixture prior to calcining. For example, in any embodiment herein, the removing may include drying the wet material mixture. In any embodiment herein, the removing may be conducted at a temperature including, but not limited to, from about 40° C. to about 150° C. For example, in any embodiment herein, the removing may occur at a temperature of about 40° C., about 50° C., about 60° C., about 70° C., about 80° C., about 90° C., about 100° C., about 110° C., about 120° C., about 130° C., about 140° C., about 150° C., or any range including and/or in between any two of the preceding values. For example, in any embodiment herein, the removing may occur at a temperature from about 40° C. to about 80° C., about 45° C. to about 65° C., about 50° C. to about 60° C., or any range including and/or in between any two of the preceding values.

In any embodiment herein, the calcined hydrogenation catalyst has a BET surface area of greater than about 15 m$^2$/g. In any embodiment herein, the calcined hydrogenation catalyst has a BET surface area greater than about 20 m$^2$/g. In any embodiment herein, the calcined hydrogenation catalyst has a BET surface area of greater than about 30 m$^2$/g. In any embodiment herein, the calcined hydrogenation catalyst has a BET surface area of greater than about 45 m$^2$/g. In any embodiment herein, the calcined hydrogenation catalyst may have a BET surface area of about 15 m$^2$/g to about 70 m$^2$/g. In any embodiment herein, the calcined hydrogenation catalyst may have a BET surface area of about 30 m$^2$/g to about 70 m$^2$/g. In any embodiment herein, the calcined hydrogenation catalyst has a BET surface area of about 45 m$^2$/g to about 70 m$^2$/g. For example, in any embodiment herein, the calcined hydrogenation catalyst has a BET surface area of about 15 m$^2$/g, about 20 m$^2$/g, about 25 m$^2$/g, about 30 m$^2$/g, about 35 m$^2$/g, about 40 m$^2$/g, about 45 m$^2$/g, about 50 m$^2$/g, about 55 m$^2$/g, about 60 m$^2$/g, about 65 m$^2$/g, about 70 m$^2$/g, or any range including and/or in between any two of the preceding values. In any embodiment herein, the calcined hydrogenation catalyst has a BET surface area of about 15 m$^2$/g to about 70 m$^2$/g, about 30 m$^2$/g to about 70 m$^2$/g, about 45 m$^2$/g to about 65 m$^2$/g, about 45 m$^2$/g to about 60 m$^2$/g, about 50 m$^2$/g to about 60 m$^2$/g, or any range including and/or in between any two of the preceding values.

The calcined hydrogenation catalyst may have a pore diameter in the range of about 150 to about 2500 Angstroms (Å). For example, in any embodiment herein, the calcined hydrogenation catalyst may have a pore diameter from about 150 Å to about 2500 Å, about 200 Å to about 2000 Å, about 225 Å to about 1500 Å, about 250 Å to about 1000 Å, about 300 Å to about 800 Å, or any range including and/or in between any two of the preceding values.

In any embodiment herein, the calcined hydrogenation catalyst may have a pore volume that is greater than or equal to 0.25 cm³/g. For example, in any embodiment herein, the calcined hydrogenation catalyst may have a pore volume of about 0.25 cm³/g, about 0.3 cm³/g, about 0.35 cm³/g, about 0.4 cm³/g, about 0.45 cm³/g, about 0.5 cm³/g, about 0.55 cm³/g, about 0.6 cm³/g, about 0.65 cm³/g, about 0.7 cm³/g, about 0.75 cm³/g, about 0.8 cm³/g, or any range including and/or in between any two of the preceding values. In any embodiment herein, the calcined hydrogenation catalyst may have a pore volume of about 0.25 cm³/g to about 0.65 cm³/g, about 0.3 cm³/g to about 0.55 cm³/g, about 0.35 cm³/g to about 0.45 cm³/g, or any range including and/or in between any two of the preceding values.

In any embodiment herein, the calcined hydrogenation catalyst may have a packed bulk density of about 0.8 g/cm³ to about 1.5 g/cm³. For example, in any embodiment herein, the calcined hydrogenation catalyst may have a packed bulk density of about 0.8 g/cm³, about 0.9 g/cm³, about 1 g/cm³, about 1.1 g/cm³, about 1.2 g/cm³, about 1.3 g/cm³, about 1.4 g/cm³, about 1.5 g/cm³, or any range including and/or in between any two of the preceding values. In any embodiment herein, the calcined hydrogenation catalyst may have a packed bulk density of about 0.8 g/cm³ to about 1.5 g/cm³, about 0.8 g/cm to about 1 g/cm³, about 0.8 g/cm³ to about 0.95 g/cm³, or any range including and/or in between any two of the preceding values.

In any embodiment herein, the calcined hydrogenation catalyst may exhibit a crush strength in an amount from about 1.5 lbs/mm to about 6.0 lbs/mm. For example, in any embodiment herein, the calcined hydrogenation catalyst may exhibit a side crush strength of about 1.5 lbs/mm, about 2.0 lbs/mm, about 2.5 lbs/mm, about 3.0 lbs/mm, about 3.5 lbs/mm, about 4.0 lbs/mm, about 4.5 lbs/mm, about 5.0 lbs/mm, about 5.5 lbs/mm, about 6.0 lbs/mm, or any range including and/or in between any two of the preceding values. In some embodiments, the catalyst may exhibit a side crush strength from about 3.5 lbs/mm to about 5.0 lbs/mm.

In any embodiment herein, the catalyst may be in an unactivated form and exhibits an X-ray powder diffraction profile with 2θ peaks at 29.6°, 35.5°, 38.7°, and 58.9°. In any embodiment herein, the catalyst may be in an unactivated form and exhibits an X-ray powder diffraction profile with 2θ peaks at 26.7°, 29.6°, 35.5°, 38.7°, 58.9°, 53.4°, 68.2°, 61.6°, 66.3°, 68.0°, 72.3°, 75.1°, and 82.9°.

In any embodiment herein, the calcined hydrogenation catalyst has a copper oxide crystallite size of about 60 Å to about 200 Å. For example, in any embodiment herein, the calcined hydrogenation catalyst may have a copper oxide crystallite size of about 60 Å, about 65 Å, about 70 Å, about 75 Å, about 80 Å, about 85 Å, about 90 Å, about 95 Å, about 100 Å, about 105 Å, about 110 Å, about 120 Å, about 125 Å, about 130 Å, about 135 Å, about 140 Å, about 145 Å, about 150 Å, about 155 Å, about 160 Å, about 165 Å, about 170 Å, about 175 Å, about 180 Å, about 185 Å, about 190 Å, about 195 Å, about 200 Å, or any range including and/or in between any two of the preceding values. In any embodiment, the calcined hydrogenation catalyst may have a copper oxide crystallite size of about 70 Å to about 165 Å.

In another aspect, the present technology provides a catalyst for hydrogenation as prepared by the method described herein in any embodiment.

Method of Use

In an aspect, methods of hydrogenating a ketone or aldehyde are provided, where the methods include hydrogenating a ketone or aldehyde by contacting the ketone or aldehyde with a hydrogenation catalyst as described herein.

In any embodiment herein, the ketone or aldehyde is a compound of Formula I:

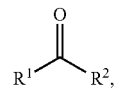

wherein $R^1$ is a substituted or unsubstituted $C_1$ to $C_{18}$ alkyl, a substituted or unsubstituted $C_3$ to $C_8$ cycloalkyl, or a substituted or unsubstituted $C_6$ to $C_{14}$ aryl; and $R^2$ is hydrogen or a substituted or unsubstituted $C_1$ to $C_{18}$ alkyl.

In any embodiment herein, $R^1$ may be a substituted or unsubstituted $C_1$ to $C_{12}$ alkyl. In any embodiment herein, $R^1$ may be a substituted or unsubstituted $C_1$ to $C_6$ alkyl. In any embodiment herein, $R^1$ may be a substituted or unsubstituted $C_6$ to $C_{14}$ aryl. For example, in any embodiment herein, $R^1$ may be a phenyl, where the phenyl may be optionally substituted with one or more of a halogen, an amine, a hydroxyl, a $C_1$ to $C_6$ alkoxy, or a $C_1$ to $C_6$ alkyl. In any embodiment herein, $R^1$ may be a phenyl substituted with a $C_1$ to $C_6$ alkyl.

In any embodiment herein, $R^2$ may be a hydrogen. In any embodiment herein, $R^2$ may be a $C_1$ to $C_6$ alkyl. For example, in any embodiment herein, $R^2$ may be a $C_1$ to $C_4$ alkyl. In any embodiment herein, $R^2$ may be a methyl. In any embodiment herein, $R^1$ and $R^2$ each independently may be a In any embodiment herein, the method may include hydrogenation of a ketone as described herein in any embodiment to the resultant aldehyde or alcohol.

In any embodiment herein, the ketone or aldehyde is a phenyl alkyl ketone or aldehyde. For example, in any embodiment herein, the ketone may be a substituted or unsubstituted phenyl alkyl ketone, such as acetophenone or 1-(4-isobutylphenyl)ethanone:

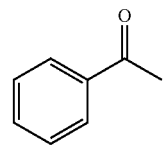

Acetophenone

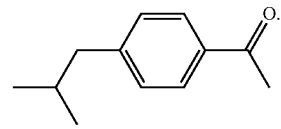

1-(4-isobutylphenyl)ethanone

Hydrogenation of such ketones may result in 1-phenylethanol and 1-(4-isobutylphenyl)ethanol, respectively.

In another aspect, methods of synthesizing butanediol are provided, where the methods include contacting a stream of dimethyl maleate with a hydrogenation catalyst as described herein in any embodiment.

In another aspect, methods of hydrogenating an ester are provided, where the methods include hydrogenating an ester by contacting the ester with a hydrogenation catalyst as described herein.

The ester may be an ester represented by Formula II:

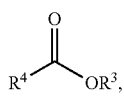

wherein $R^3$ may be a substituted or unsubstituted $C_1$ to $C_{18}$ alkyl; and $R^4$ may be hydrogen, a $C_1$ to $C_{18}$ alkyl, a $C_2$ to $C_{18}$ alkenyl, a $C_3$ to $C_8$ cycloalkyl, or a $C_6$ to $C_{14}$ aryl, wherein the $C_1$ to $C_{18}$ alkyl, $C_2$ to $C_{18}$ alkenyl, $C_3$ to $C_8$ cycloalkyl, or $C_6$ to $C_{14}$ aryl may be optionally substituted with one or more of a halogen, amine, hydroxyl, a $C_1$ to $C_6$ alkyl, or an ester represented by Formula (III),

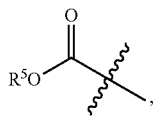

wherein $R^5$ may be hydrogen, a substituted or unsubstituted $C_1$ to $C_{18}$ alkyl, a substituted or unsubstituted $C_2$ to $C_{18}$ alkenyl, a substituted or unsubstituted $C_3$ to $C_8$ cycloalkyl, or a substituted or unsubstituted $C_6$ to $C_{14}$ aryl.

In any embodiment herein, $R^3$ may be a substituted or unsubstituted $C_1$ to $C_{12}$ alkyl. In any embodiment herein, $R^3$ may be a substituted or unsubstituted $C_1$ to $C_6$ alkyl. In any embodiment herein, $R^3$ may be a $C_1$ to $C_4$ alkyl. For example, in any embodiment, $R^3$ may be methyl, ethyl, propyl, n-butyl, sec-butyl, or tert-butyl. In any embodiment, $R^3$ may be methyl. In any embodiment, $R^4$ may be a substituted or unsubstituted $C_1$ to $C_{12}$ alkyl. In any embodiment, $R^4$ may be a substituted or unsubstituted $C_1$ to $C_6$ alkyl, a substituted or unsubstituted $C_2$ to $C_6$ alkenyl, a substituted or unsubstituted $C_5$ or $C_6$ cycloalkyl, or a substituted or unsubstituted $C_5$ or $C_6$ aryl. In any embodiment herein, $R^4$ may be a substituted or unsubstituted $C_1$ to $C_6$ alkyl. In any embodiment herein, $R^4$ may be a substituted or unsubstituted $C_2$ to $C_6$ alkenyl. For example, in any embodiment herein, $R^4$ may be a $C_2$ alkenyl substituted with an ester represented by Formula (III),

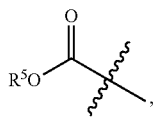

wherein $R^5$ may be a $C_1$ to $C_3$ alkyl. In any embodiment herein, $R^5$ may be methyl.

The ester may be an ester represented by Formula (IV):

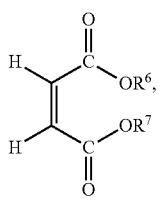

wherein $R^6$ and $R^7$ each independently may be a substituted or unsubstituted $C_1$ to $C_{12}$ alkyl, a substituted or unsubstituted $C_2$ to $C_{12}$ alkenyl, a substituted or unsubstituted $C_3$ to $C_8$ cycloalkyl, or a substituted or unsubstituted $C_6$ to $C_{14}$ aryl. In any embodiment herein, $R^6$ and $R^7$ each independently may be a $C_1$ to $C_6$ alkyl. For example, in any embodiment herein, $R^6$ and $R^7$ each independently may be a $C_1$ to $C_3$ alkyl. The ester represented by Formula (IV) may include geometric isomers; for example, in any embodiment disclosed herein, the ester of Formula (IV) may have a cis-configuration or a trans-configuration.

In any embodiment herein, $R^3$ and $R^4$ together may be represented by a $C_1$ to $C_{18}$ alkyl or $C_1$ to $C_{18}$ alkenyl such that the compound represented by Formula (II) forms a wax ester having a total of 12 to 36 carbon atoms.

The present invention, thus generally described, will be understood more readily by reference to the following examples, which are provided by way of illustration and are not intended to be limiting of the present invention.

EXAMPLES

Example 1: A series of chromium-free, copper catalysts having varying levels of copper oxide, sodium, and surface area were prepared as follows. Copper oxide, clay, calcium hydroxide (lime), alkali metal source (sodium hydroxide), manganese oxide, and silica sol were mixed and kneaded. The mixture was then extruded with an extruder and dried at a temperature range of 55° C. to 120° C. The extrudates were then calcined at 450-600° C. to a desired surface area. The catalysts had the properties outlined in Table 1, where "3F" means 3-fluted or tri-lobe.

Figure 2:
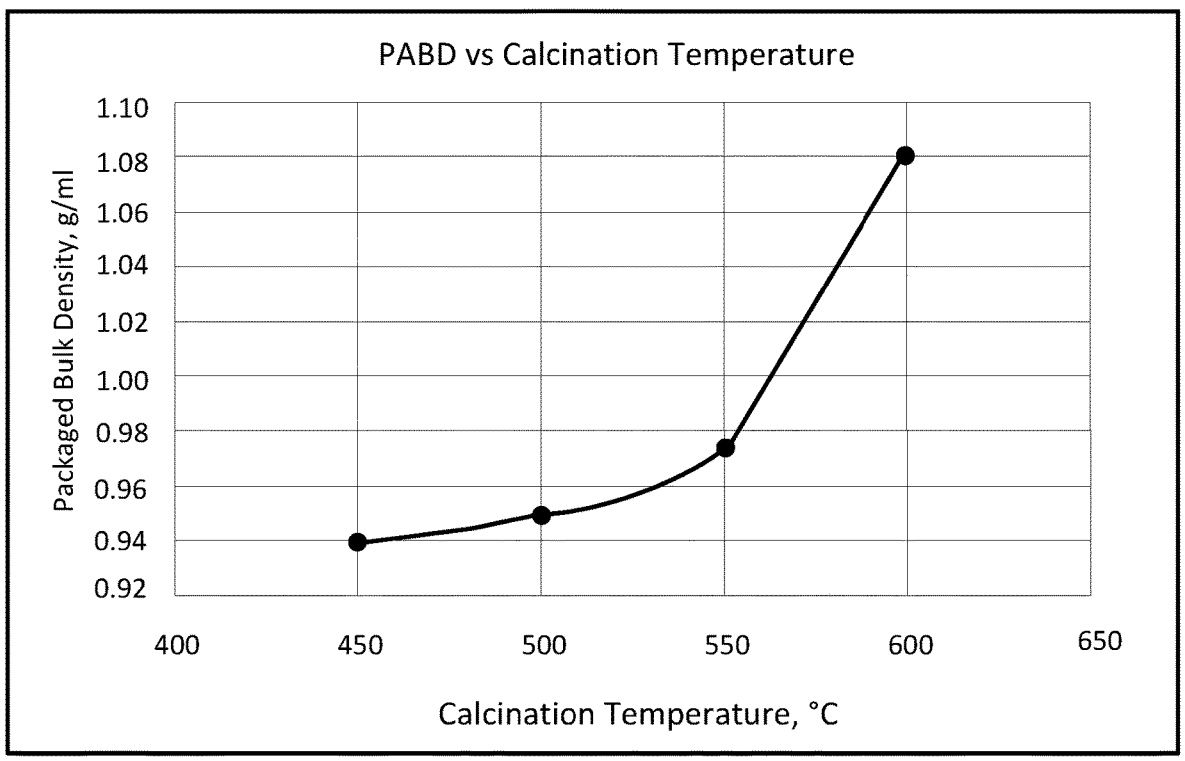
FIG. 2 illustrates a graph showing the effect of calcination temperature (° C.) on packed bulk density (g/ml) for Example Catalysts 1A-1D.
Figure 3:
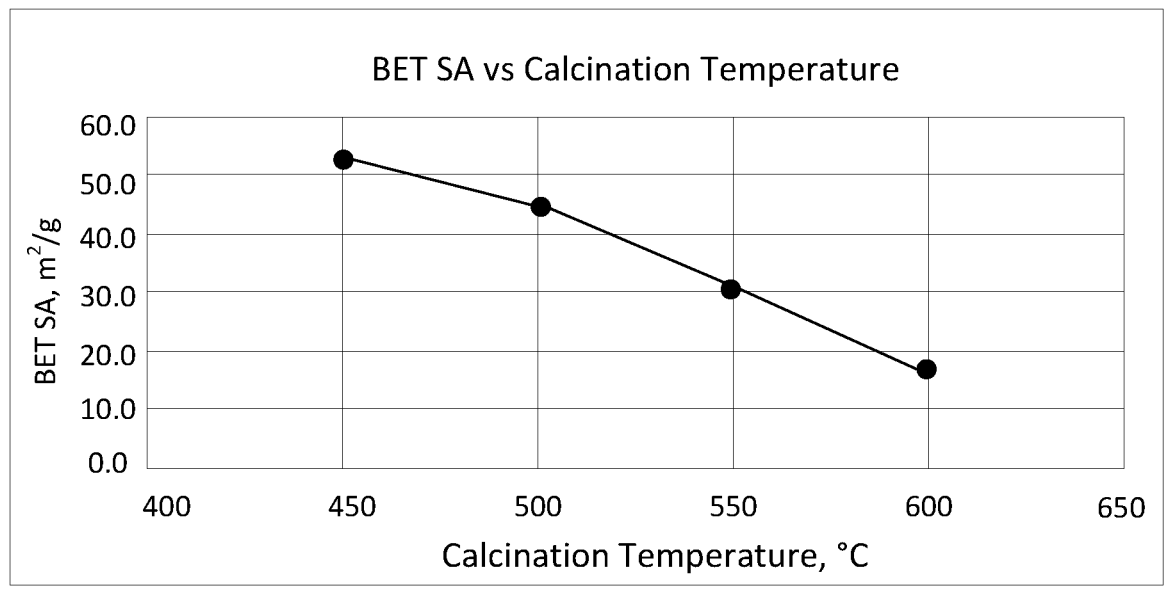
FIG. 3 illustrates a graph showing the effect of calcination temperature (° C.) on BET surface area ($m^2/g$) for Example Catalysts 1A-1D.
Figure 4:
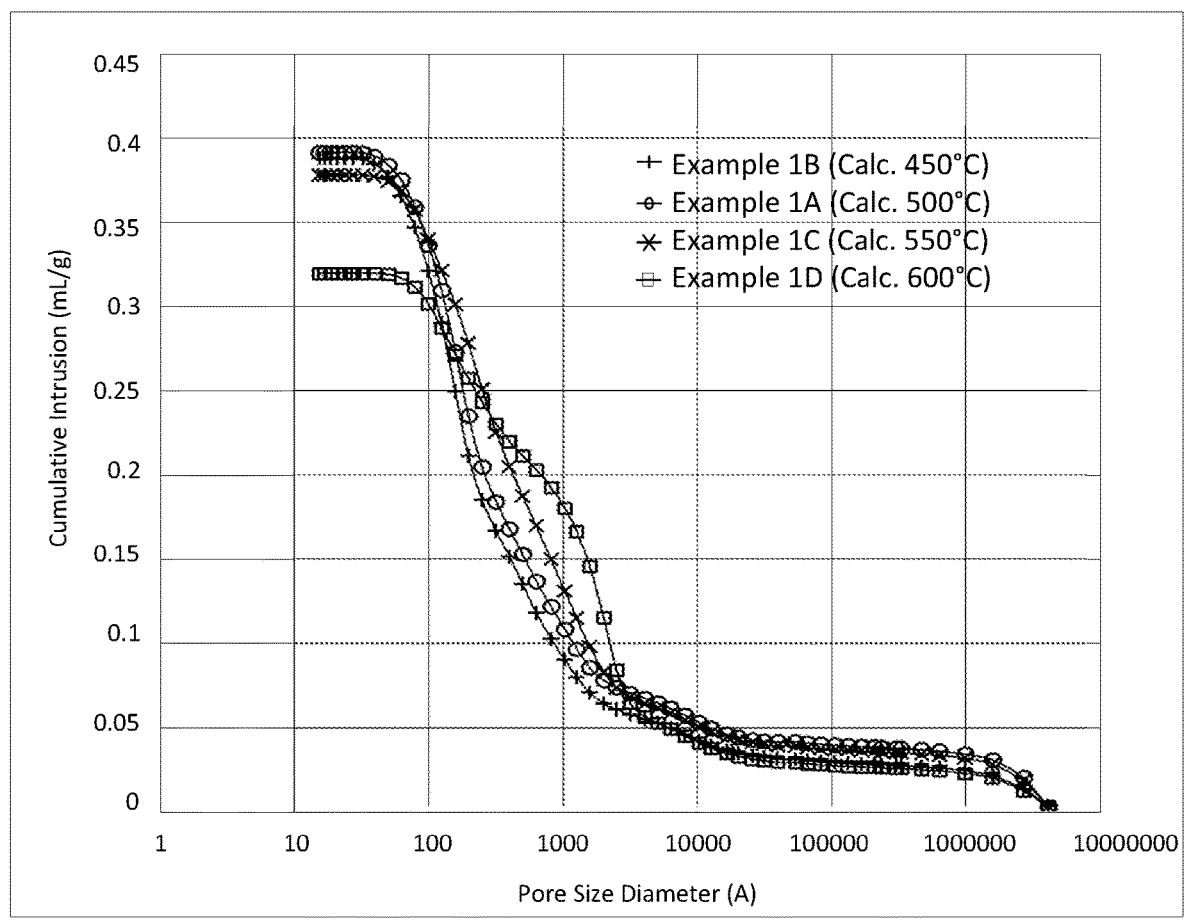
FIG. 4 illustrates a graph showing the cumulative intrusion ("pore volume," mg/L) as a function of pore diameter (Å) for Example Catalysts 1A-1D.

As shown in Table 1, the exemplary catalysts of the present technology exhibit improved crush strength and high BET surface area. In Examples 1A-1D, the effect of calcination temperature on physical properties was evaluated. As shown in FIG. 1, the catalysts of examples 1A-1D showed improved crush strength from 3.75-5.05 lb/mm at calcination temperatures from 450-600° C. FIG. 2 shows the effect of calcination temperature on packed bulk density of the catalyst, where the packed bulk density increases with an increase in calcination temperature. Conversely, increasing the calcination temperature of the catalysts resulted in a decrease in the surface area (FIG. 3). As shown in FIG. 4, the exemplary catalysts 1A-1D exhibited pore volumes of about 0.25-0.4 mL/g at pore diameters ranging from 100-1000 Å.

XRD Analysis: A PANalytical MPD X'Pert Pro diffraction system was used to collect data for exemplary catalysts 1A-1D. Cu $K_\alpha$ radiation was used in the analysis with generator settings of 45 kV and 40 mA. The optical path consisted of a 1° divergence slit, 2° anti-scatter slit, the sample, and an X'Celerator position sensitive detector. Each catalyst sample was first prepared by backpacking the sample into round mount. The data collection from the round mount covered a range from 10° to 90° 2θ using a step scan with a step size of 0.017° 2θ and a scan speed of 0.036° 2θ per second. The X'Pert Pro HighScore program was used for phase identification analysis.

Figure 5:
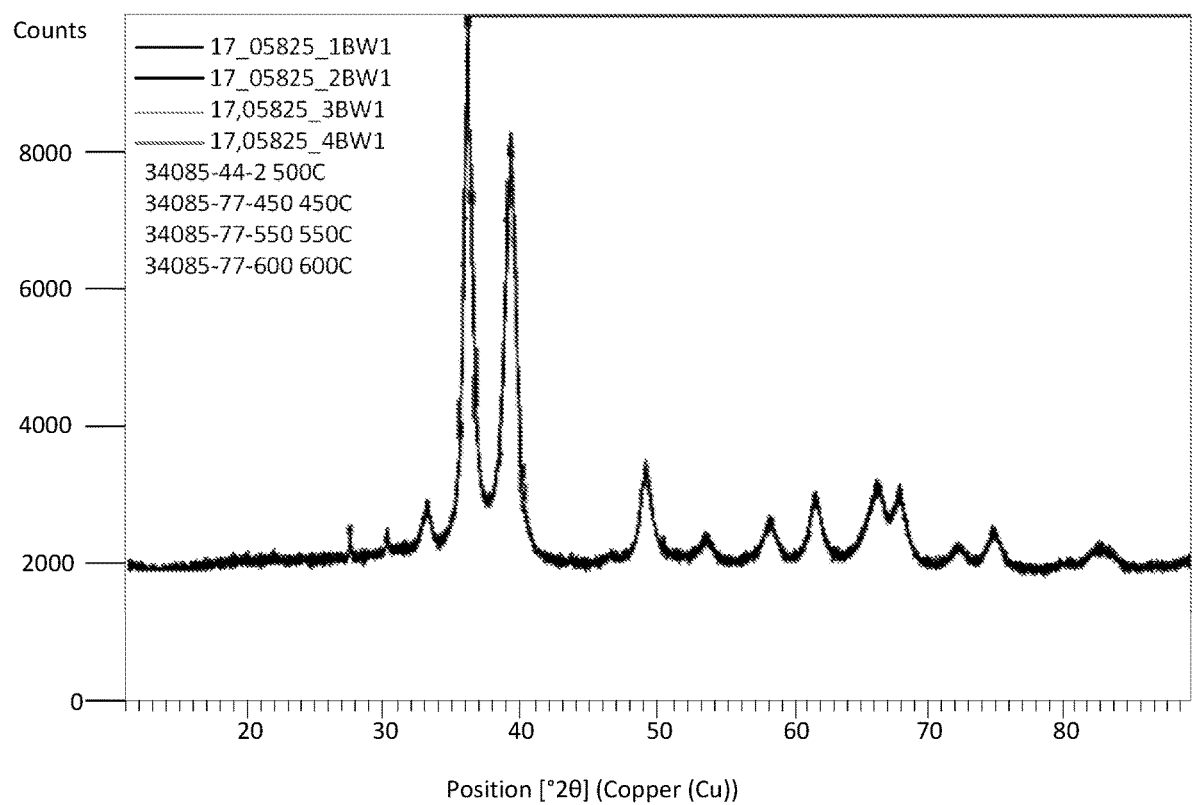
FIG. 5 illustrates a graph showing the X-ray powder diffraction spectra for Example Catalysts 1A-1D.

Monoclinic copper oxide (CuO; 00-048-1548) was the predominant phase for exemplary catalysts 1A-1D. As shown in FIG. 5, an increase in the peak intensities for this phase was observed as the calcination temperature increased. The peaks also became sharper, resulting in a consistent increase in crystallite size as calcination temperature increased as shown below:

| Example Catalyst | Crystallite Size(Å) |
|---|---|
| 1A | 81 ± 5 |
| 1B | 78 ± 5 |
| 1C | 83 ± 5 |
| 1D | 160 ± 5 |

As further shown in FIG. 5, orthorhombic sodium silicate (Na$_2$SiO$_3$; 04-008-2078) is present as a minor phase with its strongest reflection (020) matching up at 29° 2θ. Hexagonal silica (SiO$_2$; 01-075-3165) was observed around 27° 2θ. The full listing of 2θ peaks in FIG. 5 is 26.7°, 29.6°, 35.5°, 38.7°, 58.9°, 53.4°, 68.2°, 61.6°, 66.3°, 68.0°, 72.3°, 75.1°, and 82.9°.

TABLE 1

| | Ex. 1A (44-2) | Ex. 1B (77-450) | Ex. 1C (77-550) | Ex. 1D (77-600) | Ex. 1E (78-550) | Ex. 1F (79-550) | Ex. 1G (81-2) | Ex. 1H (88-2) | Ex. 1I (80-2) | Ex. 1J (108-1) | Ex. 1K | Ref. |
|---|---|---|---|---|---|---|---|---|---|---|---|---|
| % CuO @ 650° C. | 74.1 | 74.1 | 74.1 | 74.1 | 73.3 | 72.9 | 72.3 | 70.5 | 74.1 | 74.2 | 73.8 | 75.1 |
| % SiO$_2$ @ 650° C. | 13.2 | 13.2 | 13.2 | 13.2 | 13.2 | 13.2 | 13.2 | 12.4 | 13.5 | 13.2 | 13.9 | 14.7 |
| % CaO @ 650° C. | 5.7 | 5.7 | 5.7 | 5.7 | 6.2 | 6.2 | 6.2 | 6.0 | 6.3 | 5.9 | 6.4 | 3.0 |
| % MnO$_2$ @ 650° C. | 0.9 | 0.9 | 0.9 | 0.9 | 0.9 | 1.0 | 1.9 | 4.3 | 0 | 1.9 | 1.1 | 0.6 |
| % Na$_2$O @ 650° C. | 3.3 | 3.3 | 3.3 | 3.3 | 3.3 | 3.3 | 3.2 | 3.3 | 3.4 | 3.7 | 3.8 | 3.3 |
| Size/shape (3F) | 1/16" | 1/16" | 1/16" | 1/16" | 1/16" | 1/16" | 1/16" | 1/16" | 1/16" | 1/16" | 1/16" | 1/16" |
| BET surface area (m$^2$/g) | 46 | 52 | 35 | 20 | 36 | 34 | 32 | 36 | 29 | 43 | 30 | 34 |
| Hg Pore Volume (cc/g) | 0.40 | 0.39 | 0.38 | 0.32 | 0.41 | 0.41 | 0.43 | 0.37 | 0.36 | 0.38 | 0.38 | 0.29 |
| Avg. Pore Diameter (Å) | 344 | 303 | 442 | 631 | 453 | 485 | 782 | 542 | 713 | 401 | 440 | 344 |
| Packed bulk density (g/cc) | 0.95 | 0.94 | 0.97 | 1.08 | 0.93 | 0.91 | 0.87 | 0.95 | 0.95 | 0.93 | 0.99 | 1.08 |
| Crush strength, lbs./mm | 4.25 | 3.75 | 4.04 | 5.05 | 3.55 | 3.86 | 3.2 | 4.5 | 4.2 | 4.0 | 2.51 | 3.52 |
| Calcination Temp. (° C.) | 500 | 450 | 550 | 600 | 550 | 550 | 550 | 550 | 550 | 500 | 500-550 | 650 |

Example 2: Acetophenone Hydrogenation Testing. The chromium-free, copper catalysts of Example 1 were tested in a 1" outer diameter (0.839" inner diameter)×4 ft. stainless steel fixed-bed down flow reactor loaded with 40 cc (extrudates or tablets) of catalyst. An equal volume of inert 28×48 mesh α-alumina granules was loaded with the catalyst and served as interstitial packing. The reactor was also equipped with a 3/16" thermowell that housed six thermocouples, one at the inlet and five spaced equally throughout the catalyst bed which was approximately 8.25" in length. The reactor was jacketed and heated via recirculating oil bath.

Once loaded, the reactor was purged with 1 standard liter per minute ("slpm") N$_2$ for approximately 30 minutes to remove air and subsequently heated to 190° C. under N$_2$. The catalyst was activated by introducing H$_2$ in a stepwise fashion at atmospheric pressure, starting at low concentration as outlined below:
  Step 1: 12 sccm H$_2$ in 238 sccm N$_2$
  Step 2: 25 sccm H$_2$ in 225 sccm N$_2$
  Step 3: 50 sccm H$_2$ in 200 sccm N$_2$
  Step 4: 125 sccm H$_2$ in 125 sccm N$_2$
  Step 5: 200 sccm H$_2$ Each condition was typically held for a maximum of one hour or until the exotherm, as indicated by the bed temperature profile, had adequately subsided Once the reduction had been completed, the temperature was ramped down to 80° C. (reaction temperature) in 200 standard cubic centimeters per minute ("sccm") hydrogen. Once the temperature was stable at 80° C., the reactor was pressurized from atmospheric pressure to 900 psig over a time period of about two minutes by manually throttling H$_2$ into the reactor.

The feed, which was composed of 33.33 wt % acetophenone/balance ethylbenzene solvent. Activity and acetophenone conversion were measured under conditions of pressure 900 psig, temperature 80° C., feed flow rate 36.8 g/hr to give an overall liquid hourly space velocity ("LHSV") of about 1 hr$^{-1}$, and hydrogen flow rate 267 sccm. The hydrogen:acetophenone molar ratio was about 7. Product samples were collected every 24 hours on stream with experiments ranging from 48 to 96 hours. These samples were analyzed by an off-line Agilent 6890 GC equipped with a DB-WAX capillary column (30 m×0.32 mm×0.5 µm) and flame ionization detector. 1-phenylethanol is the desired product while ethylbenzene, in addition to being the solvent for the reactant, is also a side product. No other products were detected in any appreciable quantity. Commercial copper chromium based catalysts (Comp. Cat. 1 and 2) and a reference catalyst (Ref.) containing ammonia stabilized silica sol were also evaluated. The exemplary catalysts yielded the following conversions and selectivities.

The following quantities were used to assess catalyst performance and are defined as follows:

1. Percent acetophenone conversion (X)

$$X = 100 \frac{ACP_{in} - ACP_{out}}{ACP_{in}},$$

where ACP$_{in}$=Rate of acetophenone in and ACP$_{out}$=Rate of acetophenone out.

2. 1-phenylethanol space-time yield (STY), wherein STY=grams 1-phenylethanol produced per hr per volume catalyst.

3. % ethylbenzene side product in reactor effluent (% EB), $$\% \, EB = 100 \frac{EB_{out} - EB_{in}}{(EB_{out} - EB_{in}) + 1 - PE_{out}},$$

where EB$_{out}$=molar flow rate of ethylbenzene out, EB$_{in}$=molar flow rate of ethylbenzene in, and 1-PE$_{out}$=molar flow rate of 1-phenylethanol out.

TABLE 2

|  | 1A | 1B | 1C | 1D | 1E | 1F | 1G | 1H | 1I | 1K | Ref. | Comp. Cat. 1 | Comp. Cat. 2 |
|---|---|---|---|---|---|---|---|---|---|---|---|---|---|
| Catalyst Loading (g) | 38.0 | 38.1 | 40.6 | 44.8 | 39.3 | 38.6 | 37.6 | 39.6 | 39.7 | 40.5 | 44.8 | 61.76 | 62.5 |
| % acetophenone conversion | | | | | | | | | | | | | |
| T 24 hrs | 99.7 | 99.9 | 99.9 | 99.8 | 99.9 | 99.9 | 99.8 | 99.9 | 99.9 | 99.9 | 98.5 | 97.11 | 99.7 |
| T 48 hrs | 99.9 | 99.9 | 100 | 99.8 | 99.9 | 99.9 | 99.9 | 100 | 100 | 100 | 96.9 | 95.9 | 99.78 |
| T 72 hrs | — | — | — | — | — | — | — | — | — | 100 | 94.1 | 94.7 | — |
| T 96 hrs | 99.8 | — | — | — | — | — | — | — | — | 100 | 90.7 | 93.3 | — |
| Phenyl Ethanol yield (space-time-yield (STY), g/$l_{cat}$/hr) | | | | | | | | | | | | | |
| T 24 hrs | 301 | 304 | 300 | 301 | 306 | 306 | 302 | 311 | 305 | 304 | 300 | 294 | 284 |
| T 48 hrs | 298 | 303 | 299 | 302 | 304 | 303 | 304 | 305 | 303 | 302 | 293 | 288 | 295 |
| T 72 hrs | — | — | — | — | — | — | — | — | — | 302 | 284 | 284 | — |
| T 96 hrs | 301 | — | — | — | — | — | — | — | — | 303 | 275 | 279 | — |
| % Ethylbenzene | | | | | | | | | | | | | |
| T 24 hrs | 1.96 | 0.94 | 1.81 | 0.86 | — | 0.18 | 1.17 | 0.29 | 0.18 | 1.33 | 1.33 | 2.23 | 5.7 |
| T 48 hrs | 3.16 | 1.79 | 2.07 | 1.32 | 1.11 | 1.32 | 1.06 | 0.67 | 1.47 | 1.66 | 2.38 | 2.74 | 5.4 |
| T 72 hrs | — | — | — | — | — | — | — | — | — | 1.86 | 2.54 | 2.83 | — |
| T 96 hrs | 2.72 | — | — | — | — | — | — | — | — | 1.29 | 2.37 | 3.07 | — |

The data of Table 2 shows that the exemplary chromium-free copper catalysts of Examples 1A-1K, which were prepared according to the methods described herein showed improved STY for phenyl ethanol yield and catalyst life as compared to Comparative Catalysts 1 and 2 (commercial CuCr catalyst) and the Reference catalysts (ammonia silica sol catalyst). While the exemplary chromium-free copper catalysts of Examples 1A-1K showed comparable acetophenone conversion to Comparative Catalyst 2, the exemplary chromium-free copper catalysts of Examples 1A-1K exhibited high acetophenone conversion, phenyl ethanol yield, and lower production of ethylbenzene by-product compared to Comparative Catalysts 1 and 2 and Reference catalyst. In addition, the chromium-free copper catalysts of Examples 1A-1K have more stable catalytic activities, where the exemplary catalysts remain stable without losing acetophenone conversion over the testing period (up to 96 hours). In contrast, Comparative Catalysts 1 and 2 and the Reference catalyst had either lower activity or lower acetophenone conversions.

Table 3 below gives the largest temperature measured by any bed thermocouple during reduction and initial pressurization of the reactor for use according to Comparative Examples 1 and 2 and Example 1K.

TABLE 3

| | Highest Measured Bed Temperature (° C.) | |
|---|---|---|
| Catalyst | Reduction | Pressurization |
| Comp. Catalyst 1 | 191 | 280 |
| Comp. Catalyst 2 | 192 | 270 |
| Ex. 1K | 191 | 82 |

As shown in Table 3, it is evidenced by the small temperature increase from the 190° baseline temperature during reduction and the increase in temperature observed during pressurization above the 80° C. baseline temperature. The Example 1K catalyst showed a mild exotherm during pressurization, which only experiences a very small temperature increase of 2° C. that is most likely due to heat of adsorption under pressurized conditions. In contrast, Comparative Catalysts 1 and 2 both produced sharp exotherms up to 280° C. and 270° C., respectively, upon pressurization.

Without wishing to be bound by theory, the sharp exotherm are believed to be related to the existence of higher oxidation state Cr (6+). At large commercial scale reactor conditions, this large exotherm poses a safety risk, is hazardous, and creates operation difficulties.

Example 2: Dimethyl Maleate Hydrogenolysis Testing. For dimethyl maleate hydrogenolysis catalyst testing, 15 cc of the chromium-free, copper catalysts of Example 1 were loaded into a 1" outer diameter (0.834" inner diameter)×4 ft. stainless steel fixed-bed down flow reactor. An equal volume of inert 40×50 mesh α-alumina granules was loaded with the catalyst and served as interstitial packing. The reactor was also equipped with 3/16" thermowell that housed five thermocouples, two in the pre-heat zone and three spaced equally throughout the catalyst bed which was approximately 3" in length. The reactor was jacketed and heated via recirculating oil bath.

Once loaded, the reactor was purged with 4 slpm $N_2$ for approximately 30 minutes to remove air and subsequently heated to 140° C. under flowing $N_2$ at atmospheric pressure. Upon reaching 140° C., 20 sccm of $H_2$ was introduced into the $N_2$ and the catalyst subsequently heated to 220° C. At this point, the $H_2$ concentration was increased in a stepwise fashion as outlined below:
 Step 1: 40 sccm $H_2$ in 4 slpm $N_2$
 Step 2: 80 sccm $H_2$ in 4 slpm $N_2$
 Step 3: 160 sccm $H_2$ in 4 slpm $N_2$
 Step 4: 320 sccm $H_2$ in 4 slpm $N_2$
 Step 5: 640 sccm $H_2$ in 4 slpm $N_2$
 Step 6: 640 sccm $H_2$ in 2 slpm $N_2$
 Step 7: 640 sccm $H_2$ Each condition was typically held for about 20 minutes or until the exotherm, as indicated by the bed temperature profile, had adequately subsided. Once the reduction was completed, the temperature was ramped down to 200° C. where the reactor was subsequently pressurized to 900 psig under 20 standard liters per hour ("slph") $H_2$ flow. Upon completion of pressurization, the reactor was further cooled to 185° C. under 466.2 slph $H_2$.

With $H_2$ flowing at 466.2 slph and conditions stable at 185° C. and 900 psig, a 100% DMM feed was pumped into the reactor at a rate of 8.6 g/hr to give an overall LHSV of about 0.5 hr$^{-1}$. The $H_2$:DMM molar ratio was about 350, which was high enough to ensure the feed remained in the vapor phase. Product samples were collected in a liquid N$_2$ cooled trap once per day for the duration of the experiment. The samples were analyzed by an off-line Agilent 6890 GC equipped with a DB-1 capillary column (30 m×0.32 mm×3 µm) and flame ionization detector. Furthermore, off-gas from the trap was analyzed by a 5890 GC equipped an SPB-1 capillary column (30 m×0.32 mm×0.1 µm) and flame ionization detector. Off-gas was typically composed of methanol with small quantities of THF which escaped the liquid N$_2$ trap.

The following quantities were used to assess catalyst performance and are defined as follows:

1. Percent DMM conversion ($X_{DMM}$):

$$X_{DMM} = 100 \frac{DMM_{in} - DMM_{out}}{DMM_{in}}.$$

where $DMM_{in}$=Molar flow rate of DMM in and $DMM_{out}$=Molar flow rate of DMM out.

2. Percent DMS conversion ($X_{DMS}$):

$$X_{DMS} = 100 \frac{(DMM_{in} - DMM_{out}) - DMS_{out}}{(DMM_{in} - DMM_{out})},$$

where $DMM_{in}$=Molar flow rate of DMM in, $DMM_{out}$=Molar flow rate of DMM out, and $DMS_{out}$=Molar flow rate of DMS out. It is assumed that all DMM consumed in the reaction forms DMS.

3. Normalized Selectivity to Product i (% $SEL_i$):

$$\% \, SEL_i = 100 \frac{M_i}{M_{GBL} + M_{BDO} + M_{THF} + M_{n\text{-}BuOH}},$$

where $M_i$=outlet molar flow rate of product i, $M_{GBL}$=outlet molar flow rate of GBL, $M_{BDO}$=outlet molar flow rate of BDO, $M_{THF}$=outlet molar flow rate of THF, and $M_{n\text{-}BuOH}$=outlet molar flow rate of n-BuOH.

TABLE 4

|  | 1J (uncalcined) | | 1G | | | Comparative Catalyst 2 |
| --- | --- | --- | --- | --- | --- | --- |
| TOS (hr) | 22 | 46 | 22 | 46 | 70 | 21 |
| Selectivity, % | | | | | | |
| BDO | 88.3 | 87.3 | 89.2 | 89.4 | 89.5 | 87.4 |
| gBL | 10.1 | 11.4 | 8.7 | 8.5 | 8.7 | 11.2 |
| THF | 0.6 | 0.5 | 0.5 | 0.5 | 0.4 | 0.7 |
| n-BuOH | 1.0 | 0.8 | 1.6 | 1.6 | 1.5 | 0.7 |
| Activity, Conversion, % | | | | | | |
| DMM Conv. (%) | 100 | 100 | 100 | 100 | 100 | 100 |
| DMS Conv. (%) | 98.9 | 97.6 | 99.0 | 99.4 | 99.3 | 93.9 |

While certain embodiments have been illustrated and described, it should be understood that changes and modifications can be made therein in accordance with ordinary skill in the art without departing from the technology in its broader aspects as defined in the following claims.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:

1. A hydrogenation catalyst comprising:
   copper oxide;
   an alkali metal component; and
   an acid-stabilized silica;
   wherein the hydrogenation catalyst has a Brunauer-Emmett-Teller ("BET") surface area of greater than or equal to about 15 m²/g.

2. The hydrogenation catalyst of claim 1, wherein the BET surface area is from about 15 m²/g to about 70 m²/g.

3. The hydrogenation catalyst of claim 1, wherein the copper oxide is present in an amount from about 50.0 wt % to about 85.0 wt % by weight of the hydrogenation catalyst.

4. The hydrogenation catalyst of claim 1, wherein the alkali metal component comprises sodium or disodium oxide.

5. The hydrogenation catalyst of claim 1, wherein the alkali metal component is present in an amount from 0 wt % to about 8.0 wt % by weight of the hydrogenation catalyst.

6. The hydrogenation catalyst of claim 1 further comprising from about 1.0 wt % to about 18.0 wt % of calcium oxide by weight of the hydrogenation catalyst.

7. The hydrogenation catalyst of claim 1 further comprising a transition metal component selected from the group consisting of manganese, manganese oxide, zinc, nickel, cobalt, and iron.

8. The hydrogenation catalyst of claim 7, wherein the transition metal component is present in an amount from 0 wt % to about 5.0 wt % by weight of the hydrogenation catalyst.

9. The hydrogenation catalyst of claim 1, wherein the acid-stabilized silica is formed from an acid-stabilized silica solution having a pH of less than about 3.5.

10. The hydrogenation catalyst of claim 1, wherein the acid-stabilized silica is present in an amount from about 5.0 wt % to about 20.0 wt % by weight of the hydrogenation catalyst.

11. The hydrogenation catalyst of claim 1 further comprising from greater than 0 wt % to about 1.0 wt % crystalline silica by weight of the hydrogenation catalyst or about 0 wt % to about 10 wt % of a clay material.

12. The hydrogenation catalyst of claim 1, wherein the hydrogenation catalyst is a calcined and extruded hydrogenation catalyst.

13. The hydrogenation catalyst of claim 1, wherein the hydrogenation catalyst material exhibits a pore volume ≥0.25 cm³/g.

14. The hydrogenation catalyst of claim 1, wherein the hydrogenation catalyst exhibits a packed bulk density of about 0.8 g/cm³ to about 1.5 g/cm³.

15. The hydrogenation catalyst of claim 1, wherein the hydrogenation catalyst is free of, or is substantially free of, chromium or an oxide thereof.

16. The hydrogenation catalyst of claim 1, wherein the hydrogenation catalyst is in the form of a solid extrudate or tablet.

17. A method of preparing the hydrogenation catalyst according to claim 1, comprising:
   mixing a copper oxide and a clay material to obtain a dry material mixture;
   combining the dry material mixture with an aqueous acid-stabilized silica solution, a caustic material, and water to obtain a wet material mixture; and
   calcining the wet material mixture at a temperature, and for a time, sufficient to cure form a calcined hydrogenation catalyst;
   wherein the acid-stabilized silica solution has a pH of less than about 3.5.

18. A method of hydrogenating a ketone or aldehyde, comprising contacting the ketone or aldehyde with a hydrogenation catalyst comprising:
   copper oxide;
   an alkali metal component; and
   an acid-stabilized silica;
   wherein the hydrogenation catalyst has a Brunauer-Emmett-Teller ("BET") surface area of greater than or equal to about 15 m²/g.

19. A method of synthesizing butanediol, comprising:
   contacting a stream of dimethyl maleate with a hydrogenation catalyst comprising:
   copper oxide;
   an alkali metal component; and
   an acid-stabilized silica;
   wherein:
      the hydrogenation catalyst has a Brunauer-Emmett-Teller ("BET") surface area of greater than or equal to about 15 m²/g; and
      the silica is formed from an acid-stabilized silica solution having a pH of less than about 3.5.

20. A method of hydrogenating an ester, comprising contacting the ester with a hydrogenation catalyst comprising:
   copper oxide;
   an alkali metal component; and
   an acid-stabilized silica;
   wherein the hydrogenation catalyst has a Brunauer-Emmett-Teller ("BET") surface area of greater than or equal to about 15 m²/g.

* * * * *